United States Patent
Nokihara et al.

(10) Patent No.: US 9,857,369 B2
(45) Date of Patent: *Jan. 2, 2018

(54) BIOCHIP SUBSTRATUM AND METHOD FOR PRODUCTION THEREOF

(71) Applicants: HIPEP LABORATORIES, Kyoto-shi, Kyoto (JP); NIPPON LIGHT METAL COMPANY, LTD., Tokyo (JP)

(72) Inventors: Kiyoshi Nokihara, Kyoto (JP); Akiyoshi Hirata, Kyoto (JP); Yasuo Oka, Shizuoka (JP); Yasushi Takebayashi, Shizuoka (JP)

(73) Assignees: HIPEP LABORATORIES, Kyoto-shi (JP); NIPPON LIGHT METAL COMPANY, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/338,205

(22) Filed: Jul. 22, 2014

(65) Prior Publication Data

US 2014/0336081 A1  Nov. 13, 2014

Related U.S. Application Data

(63) Continuation of application No. 13/001,923, filed as application No. PCT/JP2009/061908 on Jun. 30, 2009, now Pat. No. 8,822,607.

(30) Foreign Application Priority Data

Jun. 30, 2008 (JP) ................................ 2008-171322

(51) Int. Cl.
*G01N 33/545* (2006.01)
*C12Q 1/68* (2006.01)
(Continued)

(52) U.S. Cl.
CPC .............. *G01N 33/545* (2013.01); *C08J 3/28* (2013.01); *C12Q 1/6837* (2013.01);
(Continued)

(58) Field of Classification Search
CPC ........... G01N 33/545; G01N 33/54353; C12Q 1/6837; C08L 79/02; C08L 71/02
See application file for complete search history.

(56) References Cited

U.S. PATENT DOCUMENTS 8,551,765 B2   10/2013  Okamura et al.
8,822,607 B2 * 9/2014  Nokihara ............. C12Q 1/6837
                                                        427/249.6

(Continued)

FOREIGN PATENT DOCUMENTS

EP   0 410 323 A2   1/1991
EP   1 557 364 A1   2/2008
(Continued)

OTHER PUBLICATIONS

Sun, B., et al., "Covalent photochemical functionalization of amorphous carbon think films for integrated real-time biosensing," Langmuir, 2006, 22, 9598-9605.*

(Continued)

*Primary Examiner* — Nicholas Hill
(74) *Attorney, Agent, or Firm* — Birch, Stewart, Kolasch & Birch, LLP

(57) ABSTRACT

A substrate for biochips which has a high probe loading amounts and a uniform immobilization density, and which further has a high detection sensitivity and a high reproducibility by preventing a non-specific adsorption of proteins, when used as a substrate for biochips for immobilizing probes composed of biologically relevant substances such as proteins and nucleic acids, is disclosed. Amino groups can be bound to the surface of the substrate uniformly, at a high (Continued)

density and stably by covalently immobilizing an amino group-containing polymer on the surface of the substrate. The probe immobilization rate is high and immobilizing density was uniform by immobilizing a probe composed of a biologically relevant substance such as a protein or nucleic acid by utilizing the amino groups. Further, detection sensitivity and reproducibility are high by inhibiting non-specific adsorption of proteins.

24 Claims, 3 Drawing Sheets

(51) Int. Cl.
*G01N 33/543* (2006.01)
*C08J 3/28* (2006.01)
*B01L 3/00* (2006.01)

(52) U.S. Cl.
CPC . *G01N 33/54353* (2013.01); *G01N 33/54393* (2013.01); *B01J 2219/0061* (2013.01); *B01J 2219/00527* (2013.01); *B01J 2219/00596* (2013.01); *B01J 2219/00605* (2013.01); *B01J 2219/00612* (2013.01); *B01J 2219/00635* (2013.01); *B01J 2219/00637* (2013.01); *B01L 3/50* (2013.01); *Y10T 428/273* (2015.01)

(56) References Cited

U.S. PATENT DOCUMENTS

| | | | | |
|---|---|---|---|---|
| 2002/0197417 | A1* | 12/2002 | Nakamura | C23C 16/30 427/585 |
| 2003/0124332 | A1 | 7/2003 | Mao et al. | |
| 2003/0143592 | A1* | 7/2003 | Kawamura | C08L 51/10 435/6.12 |
| 2004/0023413 | A1* | 2/2004 | Opalsky | C12N 11/06 506/9 |
| 2005/0239102 | A1* | 10/2005 | Verdine | C07H 21/00 435/6.12 |
| 2005/0244898 | A1* | 11/2005 | Cohen | C12N 11/00 435/7.2 |
| 2008/0146459 | A1 | 6/2008 | Iwakura et al. | |
| 2008/0161200 | A1* | 7/2008 | Yu | C40B 40/08 506/13 |
| 2008/0261827 | A1 | 10/2008 | Iwakura et al. | |
| 2009/0209436 | A1* | 8/2009 | Larman | B01J 19/0046 506/9 |
| 2009/0258440 | A1* | 10/2009 | Bunch | G01N 33/54353 436/518 |

FOREIGN PATENT DOCUMENTS

| | | |
|---|---|---|
| JP | 2004-347317 A | 12/2004 |
| JP | 2005-195465 A | 7/2005 |
| WO | WO 2004/007710 A1 | 1/2004 |
| WO | WO 2006-059727 A1 | 6/2006 |
| WO | WO 2006-126568 A1 | 11/2006 |

OTHER PUBLICATIONS

Smirnovas, V., et al., "Thermodynamic properties underlying the alpha-helix-to-beta-sheet transition, aggregation, and amyloidogenesis of polylysine as proved by calorimetry, densimetry, and ultrasound velocimetry," J. Phys. Chem. B Letters, 2005, 109, 19043-19045.*

International Search Report, PCT/JP2009/061908, dated Aug. 25, 2009.

Ito et al., "Micropatterned Immobolization of Epidermal Growth Factor to Regulate Cell Function", Bioconjugate Chem., vol. 9, 1998, pp. 277-282.

Poly(allylamine) solution, product data from Aldrich, Downloaded on Dec. 18, 2013.

Poly(ethylene glycol), molecular weight 600, product data from Aldrich, Downloaded on Dec. 18, 2013.

Search Report dated Jun. 30, 2011, in European Patent Application No. 09773454.5.

Sun et al., "Covalent Photochemical Functionalization of Amorphous Carbon Thin Films for Integrated Real-Time Biosensing", Langmuir, vol. 22, 2006, pp. 9598-9505.

Zhang et al., "Proteins and cells on PEG immobilized silicon surfaces", Biomaterials, vol. 19, 1998, pp. 953-960.

* cited by examiner

After first washing

After second washing

After first washing

After second washing

Before washing

After washing

Before washing

After washing

BIOCHIP SUBSTRATUM AND METHOD FOR PRODUCTION THEREOF

CROSS-REFERENCE TO RELATED APPLICATIONS

This application is a continuation application of U.S. application Ser. No. 13/001,923, filed on Mar. 2, 2011, which is the National Phase of International Application No. PCT/JP2009/061908 filed on Jun. 30, 2009, which claims priority to Japanese Patent Application No. 2008-171322 filed on Jun. 30, 2008, all of which are hereby expressly incorporated by reference into the present application.

TECHNICAL FIELD

The present invention relates to a substrate for biochips on which substrate biologically relevant substances such as proteins, nucleic acids, peptide derivatives, sugar chains and derivatives thereof, natural products and small molecule compounds are to be immobilized as probes; to a method thereof; and to a biochip using the same.

BACKGROUND ART

Biochips wherein nucleic acids or proteins are immobilized on the surface of a planar substrate include those produced by: the Affymetrix method in which oligonucleotides are synthesized on the surface of a substrate by using photolithography; and the Stanford method in which probe nucleic acids or probe proteins which are prepared in advance are spotted and immobilized on the surface of the substrate. It is well-known that with either type of biochips, fluorescence is detected after a biochemical reaction with a target, and then identification of molecules or diagnosis based on the change in the intensity thereof or pattern thereof is performed. Among the two methods, the Affymetrix method has a drawback in that it is difficult to immobilize stably or synthesize a long oligonucleotide because the synthesize is performed on the surface of the substrate and the cost is high. In the Stanford method, very small spots of materials such as probe nucleic acids and probe proteins are placed on the surface of the substrate, and a "non-covalent type" polylysine or a "covalent type" amino group, aldehyde group, silano group or epoxy group is provided in order to immobilize molecules to be recognized by adsorption or covalent bond. However, there exists a problem that the non-covalent type has a poor stability and a short storage life, and that the amount of probes immobilized decreases with time.

In the covalent type, the amount of functional groups is not uniform over the plane, and the density of probes is non-uniform, and therefore a uniform SN ratio cannot be obtained. The density of the functional groups is also not sufficient, and not sufficient particularly for the density of the proteins immobilized to achieve a reproducibility. Further, the amount of biological substances, particularly proteins, which are non-specifically adsorbed is large, and thus the S/N ratio decreases. Therefore, a substrate which satisfies both of the detection sensitivity and reproducibility cannot be obtained.

PRIOR ART LITERATURES

Patent Literatures

[Patent Literature 1] JP 2001-128683 A
[Patent Literature 2] Japanese Translated PCT Patent Application Laid-open No. 2005-510440

SUMMARY OF THE INVENTION

Problems to be Solved by the Invention

An object of the present invention is to provide a substrate for biochips which has a high probe immobilization rate and a uniform immobilization density, and which further has a high detection sensitivity and a high reproducibility by inhibiting a non-specific adsorption of a protein, when used as a substrate for biochips the immobilizing probes composed of biologically relevant substances such as proteins and nucleic acids.

Means for Solving the Problems

The present inventors intensively studied to discover that amino groups can be bound to the surface of the substrate uniformly, at a high density and stably by immobilizing covalently an amino group-containing polymer on the surface of the substrate, and that probe immobilization rate is high and immobilizing density is uniform by immobilizing a probe composed of a biologically relevant substance such as a protein or nucleic acid by utilizing the amino groups, and further, detection sensitivity is high and reproducibility is high by inhibiting non-specific adsorption of proteins, thereby completing the present invention.

That is, the present invention provides a substrate for biochips, comprising an amino group-containing polymer covalently immobilized on its surface. The present invention also provides a biochip comprising a biologically relevant substance covalently bound directly or via a linker to the amino group of the substrate for biochips. The present invention further provides a method of producing the above-described substrate for biochips according to the present invention, the method comprising coating the surface of the substrate with the amino group-containing polymer; and subsequently irradiating the surface of the substrate with light under reduced pressure or under an inert gas atmosphere. The present invention still further provides a method of producing the above-described substrate for biochips according to the present invention, the method comprising a plasma irradiation or a light irradiation on the surface of the substrate; and immediately thereafter, dipping the substrate in a solution of the amino group-containing polymer.

Effects of the Invention

In the substrate for biochips of the present invention, amino groups can be bound to the surface of the substrate uniformly, at a high density and stably by immobilizing covalently an amino group-containing polymer on the surface of the substrate, and probe immobilization rate is high and immobilizing density is uniform by immobilizing a probe composed of a biologically relevant substance such as a protein or nucleic acid by utilizing the amino groups, and further, detection sensitivity is higher and reproducibility is higher by prevention of non-specific adsorption of proteins.

BEST MODE FOR CARRYING OUT THE INVENTION

Figure 1:
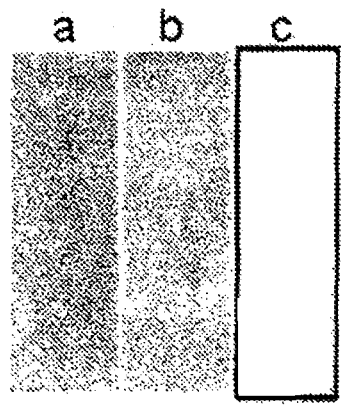
FIG. 1 shows images (a, b) of surfaces which are surfaces of the substrates produced in Example 1 modified by a fluorescence label which binds to an amino group, and an image (c) of a surface which is the surface of the substrate produced in Example 1 modified by a fluorescence labeling which binds to an amino group.

A substrate for biochips of the present invention (hereinafter, also simply referred to as "a substrate" for short) is characterized in that an amino group-containing polymer(s) is(are) covalently immobilized on the surface of the substrate. Here, "an amino group" means a primary amino group, i.e., $-H_2$. The amino group-containing polymer is preferably the one wherein each of 50% or more, more preferably 90% or more, still more preferably 99% or more of constituent units which constitute the amino group-containing polymer has at least one amino group at the state before being immobilized. Since such an amino group-containing polymer has many amino groups in one molecule, amino groups are bound uniformly at high density to the surface of the substrate via the amino groups. The amino group-containing polymer is preferably the one which is formed by addition polymerization of amino group-containing vinyl monomer, and polyallylamine (PAA) is particularly preferred. When the amino group-containing polymer is covalently bound to the substrate, the amino group-containing polymer is not removed even when the substrate is washed by stirring in purified water for one hour as specifically described in the below-mentioned Examples, and it is possible to quantify the amino groups by a method in which bromide ions released by treatment with mercaptoethanol after bromoacetylating amino groups are quantified by ion chromatography as described in the below-mentioned Examples. It is also possible to directly confirm the amino groups by X-ray photoelectron spectroscopy (XPS).

The average molecular weight (weight-average molecular weight) of the amino group-containing polymer is preferably 1000 or more, and more preferably 2000 or more in terms of PAA from the viewpoint of better attaining the effect of the present invention. Here, "in terms of PAA" means converting the number of molecular weight based on the number of amino groups in one molecule (same as below). On the other hand, the upper limit of the molecular weight of the amino group-containing polymer is not particularly limited as long as handlings such as solubility and stability of the coating solution are not problematic, and preferably 60,000 or less, more preferably 6,000 or less.

The amount of the amino group-containing polymer immobilized on the surface of the substrate is preferably 4 $\mu g/cm^2$ or more in terms of polyallylamine. When the amount of the amino group-containing polymer immobilized on the surface of the substrate is less than 4 $\mu g/cm^2$, the amount of amino groups on the surface of the substrate is small, and the amount of test samples or probes is not sufficient. On the other hand, the amount of the amino group-containing polymer immobilized on the substrate is preferably 40 $\mu g/cm^2$ or less. When the amount of the amino group-containing polymer immobilized on the substrate is more than 40 $\mu g/cm^2$, a polymer layer tends to be removed, and the immobilization of the test samples or probes may be deteriorated.

Non-specific adsorption of proteins hardly occur even in the case where probes are immobilized on the substrate on which only amino group-containing polymer is immobilized. However, when it is desired that non-specific adsorption of proteins or the like by hydrophobic bonding or the like be further prevented, a hydrophilic polymer in addition to the amino group-containing polymer may be immobilized covalently on the surface of the substrate. As the hydrophilic polymer, those which have low reactivity with an amino group are used. Examples of the hydrophilic polymer include polyethers, polyacrylamides and agarose. Among polyethers, polyethylene glycol (hereinafter, also referred to as "PEG" for short) whose molecular weight distribution is controlled may be particularly employed, and preferred because the stability is high and polyethylene glycol does not inactivate biological substances. The average molecular weight of the hydrophilic polymer is preferably such that the reactivity with a linker or probe of the amino group-containing polymer is not inhibited, and is 1000 to 10,000, and more preferably 1000.

When a hydrophilic polymer is immobilized, in order to ensure a uniform distribution of the amino groups, it is preferred that amino group-containing polymer and the hydrophilic polymer be uniformly mixed. That is, a uniform mixture of amino group-containing polymer and the hydrophilic polymer is preferably immobilized on the surface of the substrate with the method mentioned below.

Hydrophilic polymer may not be immobilized because it is an optional ingredient. However, in cases where a hydrophilic polymer is immobilized, the amount of the hydrophilic polymer immobilized is preferably equal to or less than the amount of the amino group-containing polymer immobilized from the viewpoint of binding sufficient amount of amino groups on the surface of the substrate. Also in cases where both amino group-containing polymer and hydrophilic polymer are immobilized, the amount of the amino group-containing polymer immobilized on the surface of the substrate is preferably 4 $\mu g/cm^2$ or more in terms of polyallylamine as described above. On the other hand, the total amount of amino group-containing polymer and hydrophilic polymer immobilized is 40 $\mu g/cm^2$ or less as in cases where the amino group-containing polymer alone is immobilized. The hydrophilicity of the substrate can be adjusted by the amount of hydrophilic polymer immobilized.

The surface of the substrate may be the one to which the above-described polymer (which, when simply referred to as "polymer", means the amino group-containing polymer, or a mixture of amino group-containing polymer and hydrophilic polymer unless otherwise specified) can be covalently bound, and is preferably composed of a material which easily generates radicals by light irradiation or plasma irradiation. At least the surface of the substrate is preferably composed of carbon or plastic because a bond in which at least one of the atoms forming the bond is a carbon atom, such as C—C, C—O or C—H easily generates radicals by light irradiation or plasma irradiation. As the carbon, amorphous carbon or diamond-like carbon is preferred. As the plastic, any plastic may be used as long as the plastic contains carbon, and examples thereof include acrylic resins, polystyrene and polyethylene terephthalate from the viewpoint of rigidity and workability. In order to promote the accuracy of measurement when used as a biochip, the surface of the substrate is preferably as flat as possible and may be polished as required. The surface roughness Ra is preferably 2 nm or less and more preferably about 1 nm.

The material of the substrate body is not limited in any way as long as at least the surface of the substrate is formed by a material described above. The whole substrate can be constituted by the above-described material which forms the surface of the substrate, such as amorphous carbon or plastic, or diamond carbon or the like can be coated on the substrate body. The substrate body can be formed by any one of carbon, metal, glass, ceramics or plastic, or can be formed by a complex thereof. When carbon or plastic is not employed, the above-described polymer may be immobilized on the substrate after the treatment of providing a carbon layer thereon. Among these method, a method of forming the whole substrate with carbon is particularly preferred in view of chemical resistance, heat resistance, and absence of auto-luminescence. As the metal, those wherein a carbon or diamond-like carbon layer is provided on the surface of aluminum, stainless steel, iron and steel, copper or the like, or alloy thereof by a treatment method such as spattering, CVD, PVD or the like in order to ensure a covalent bond with the polymer may be employed. Aluminum on the surface of which nickel-phosphate plating or the like is treated in order to improve corrosion resistance and surface rigidity and then the above-described carbon layer is provided may be employed as the substrate material. Glass and ceramics are materials generally employed as a material for biochips. A layer of carbon or diamond-like carbon may be further provided on the surface of the material by a treatment method such as spattering, CVD or PVD for the purpose of ensuring covalent bonds with the polymer, and for the purpose of preventing excess adsorption of protein test samples.

Methods of covalently binding carbon or plastic on the surface of the substrate with the polymer include the first method in which the polymer is applied on the surface of the substrate, and then radicals are generated on the surface of the carbon by light irradiation to attain the covalent bonds; and the second method in which radicals are generated on the surface of the carbon by plasma treatment or light irradiation, and then the radicals are reacted with the polymer to attain the bonds.

The first method is a method in which a polymer solution is applied on the surface of the substrate, and then radicals are generated on the surface of the carbon by light irradiation to attain the covalent bonds. In this method, as the light to be irradiated, ultraviolet rays having a wavelength of about 150 nm to 260 nm, for example, a wavelength of 184 nm or 254 nm may be employed. By the light having such a wavelength, the C—C, C—O and C—H bonds are cleaved to generate radicals. At this time, oxygen molecules and water molecules in the air are also decomposed to generate oxygen radicals and ozone, and at the same time, oxidative destruction of the substrate material carbon and polymer occurs, which causes inhibition of covalent bond formation. In order to prevent this, in the production method of the present invention, light irradiation is preferably performed under reduced pressure or under an inert gas atmosphere. To prevent this, vacuuming may be performed at a degree of vacuum of −0.05 MPa or less, preferably −0.08 MPa or less based on atmosphere pressure (0 MPa). As an inert gas, a rare gas element such as argon or helium is employed which is hard to generate radicals even when a light is irradiated. Light dose may be any amount as long as the amount is the one which is needed for the polymer to be bound covalently, and is usually about 1 to 6 joules, preferably about 2 to 4 joules per 1 $cm^2$ of the surface of the substrate. For example, an ultraviolet ray of 18.5 mW per 1 $cm^2$ of the surface of the substrate is irradiated usually for 1 to 5 minutes, and preferably for 2 to 4 minutes. The amount of the polymer applied is an amount by which the above-described amount of the immobilized polymer is attained. The concentration of the polymer solution may be any concentration as long as a required coating amount of the polymer can be attained and the solution can be uniformly applied, and is preferably about 0.5% to 3% by mass.

In the second method, radicals are generated on the surface of the carbon by plasma irradiation or light irradiation, and immediately, the radicals generated on the surface of the substrate are brought into contact with a polymer solution, so as to allow the reaction with the polymer. Plasma process can be carried out under reduced pressure or under atmospheric pressure, and the process can also be carried out by using reactive plasma in which argon gas, carbon dioxide gas, ammonium gas, water vapor or the like is introduced as required. The plasma dose is that attained by irradiation under conditions of high frequency output of 1 to 100 W, reactant gas flow of 5 to 20 $cm^3$/min and dose time of 10 to 120 seconds, and more preferably, high frequency output of 1 to 10 W, reactant gas flow of 5 to 15 $cm^3$/min and dose time of 20 to 90 seconds. The light dose is any amount as long as the amount is the one needed for the polymer to be covalently bound, and is usually about 3 to 35 joules per 1 $cm^2$, preferably about 5 to 16 joules per 1 $cm^2$ of the surface of the substrate in terms of energy amount. For example, an ultraviolet ray of 18.5 mW per 1 $cm^2$ of the surface of the substrate is irradiated usually for 3 to 30 minutes, and preferably for 5 to 15 minutes. The light irradiation can be carried out under atmospheric pressure. In cases where the polymer is immobilized only by the second method, it is required to allow the generated radicals to immediately be in contact with a polymer solution before the generated radicals disappear. From the viewpoint of allowing the generated radicals to immediately be in contact with a sufficient amount of polymer solution, roll coating, spray coating and dip coating (dipping) are preferred.

Polymer immobilization can be carried out by conducting either of the above-described first method or the second method. It is also possible to combine the first method and the second method, that is, to carry out the first method after carrying out the second method. That is, plasma irradiation or light irradiation is performed on the surface of the substrate, and then a polymer solution is applied, and light irradiation may be further performed, which is a preferred method. In this case, there is no problem even when the generated radicals by the second method decrease or disappear, because further light irradiation is performed after applying a polymer solution. Also in this case, at least the effect of improving a wettability of the polymer solution is attained by the second method which is conducted in advance. The second method is therefore regarded as a pre-treatment of the application of the polymer solution.

For the application of the polymer on the surface of the substrate, a general method may be employed, and is not particularly limited as long as the method is the one in which the coating amount of the polymer can be controlled. For example, the method may be selected from roll coating, spray coating, spin coating, dip coating and the like and carried out.

The thus obtained substrate of the present invention has amino groups on the surface thereof uniformly and at a high density. By using these amino groups to immobilize biologically relative substances by covalent bonds, biochips may be constituted. Biologically relevant substances may be any substance which is employed as probes on biochips, and examples thereof include any polypeptides (including natural or synthesized proteins and oligopeptides), nucleic acids (including DNAs and RNAs and artificial nucleic acids), sugars, lipids, complexes thereof (e.g., sugar proteins) and derivatives thereof (e.g., modified proteins or nucleic acids).

The biologically relevant substances may be bound covalently to the amino groups directly or may be bound to the amino groups via a desired linker. Because substrates for biochips per se which have amino groups on the surface thereof are widely commercially available, it is easy to bind biologically relevant substances to the amino groups covalently by a well-known conventional method. When the biologically relevant substance is one having a carboxyl group or the like which binds to an amino group, such as proteins, the substance may be bound to the substrate directly. When the biologically relevant substance is one which does not have such a functional group or when desired, the substance may be bound to the substrate via a linker. The linker is also well-known. For example, those which have a carboxyl group on one end and, for example, a maleimide group on the other end are widely used.

EXAMPLES

The present invention will now be described more concretely by way of Examples and Comparative Examples thereof. However, the present invention is not restricted to the Examples below. Before the description of each of examples, evaluation methods of the produced substrates will be described.

[Evaluation of Uniformity of Amount of Amino Groups on Surface of Substrate]

The uniformity of the amino groups on the surface of the substrate was evaluated by binding fluorescent molecules to the amino groups by coating the whole surface of the substrate with a solution of fluorescent molecules (TAMRA) activated such that the molecules had a reactivity with amino groups; and then scanning the surface by a fluorescent scanner. Concretely, a substrate was dipped in a solution containing 10 mM N,N,N',N'-tetramethyl-(5 or 6)carboxyrhodamine (TAMRA), 10 mM HBTU (2-1H[benzotriazol-1-yl]-1,1,3,3,tetramethyloronium-hexafluorophosphate), 20 mM DIEA (diisopropylethylamine) DMF (dimethylformamide) solution and stirred at room temperature for one hour, whereby TAMRA was bound to amino groups. Subsequently, excess TAMRA was washed off by methanol and then the substrate was dried under reduced pressure. The thus obtained substrate was scanned (Power 40%, Resolution 30 μm, PMT 65%, excitation 532 nm, emission 573 nm) by a fluorescent scanner (Hitachi Software Engineering Co., Ltd., CRBIO IIe), and the uniformity was evaluated by the obtained image and luminance distribution histogram.

[Evaluation of Amount of Amino Groups on Surface of Substrate]

The amount of amino groups on the surface of the substrate was measured by a method in which bromide ions released by bromoacetylating the surface of the substrate and then treating the surface with mercaptoethanol are quantified by ion chromatography (Shimadzu Corporation). Concretely, a substrate was dipped in a solution of 10 mM anhydrous bromoacetic acid (prepared by mixing bromo acetic acid and DCC [dicyclohexylcarbodiimide] in dioxane) and 10 mM pyridine in dioxane and shaken for one hour, thereby bromoacetylating the amino groups. Subsequently, excess bromoacetic acid was washed away with methanol, and then, the substrate was dried under reduced pressure. Further, the substrate was dipped in a 10 mM aqueous mercaptoethanol solution and shaken for one hour, thereby allowing bromide ions to be released. Ten μL of the solution containing the bromide ions was aliquoted and subjected to ion chromatography to quantify the concentration of bromide ions, thereby calculating the amount of amino groups per unit area from the surface area of the substrate.

[Evaluation of Probe Immobilization]

As a linker between the probe and the substrate, EMCA (6-maleimide capronic acid) was introduced. After converting EMCA to symmetric anhydride with DCC, pyridine was added thereto in an amount to attain a concentration of 10 mM, and a PAA-immobilized amorphous carbon substrate was immersed for one hour in the obtained solution. A solution of a synthetic peptide (amino acid sequence: GLQQLARALRRLAQAGC (SEQ ID NO: 1)) as a probe having an α-helix structure labeled with a fluorescent molecule TAMRA, at a concentration of 10 μM in 1% aqueous acetic acid solution, was spotted (arrayed) on the surface of the above-described substrate. Further, in order to cap excessive EMCA, the substrate was dipped in 10 mM mercaptoethanol solution, then washed with methanol and subjected to spin drying, and then, fluorescence was measured by a fluorescence scanner to confirm the existence of the probes. Further, the substrate was washed with aqueous 50% isopropanol solution, and then, dried in vacuum, and fluorescence was measured again by a fluorescence scanner to confirm that the probe was remained (i.e., the probe which was immobilized).

[Evaluation of Degree of Adsorption of Proteins]

A solution of bovine serum albumin (BSA) as a protein, labeled with fluorescent molecule TAMRA at a concentration of 0.01% in phosphate buffer was spotted on the surface of the substrate and the substrate was allowed to stand for one hour. The thus obtained substrate was washed with aqueous 50% isopropanol solution and then subjected to spin drying, followed by measurement by a fluorescence scanner. The state of adsorption of the protein was evaluated by fluorescent images.

Example 1

1. Production of Substrate for Biochips
(1) Substrate and Ultraviolet Treatment Using, as a substrate material, an amorphous carbon plate (25.0×75.0 mm, tolerance±0.1 mm, plate thickness 1.000 mm, tolerance±0.025 mm) which was polished such that the surface roughness Ra was 1 nm, a 15-minute ultraviolet irradiation (18.5 mW/cm$^2$, 254 nm) was performed by an ultraviolet irradiation apparatus (SEN LIGHTS Co., Ltd., Photo Surface Processor PL 16-110).

(2) Application of Polymer Solution and Immobilization of Polymer

PAA (average molecular weight: 3,000) was dissolved in ethanol at a concentration of 1% by mass, and the obtained solution was used as a coating solution. A suitable amount of the PAA coating solution was aliquoted with a pipette and dropped on the surface of the substrate material, and the solution was spread over the entire surface of the substrate material with a Baker applicator whose coating thickness was set at 3 mil (about 0.076 mm) so as to attain a coating amount of PAA of 20 µg/cm$^2$. After volatilization of the solvent, the substrate was dried under vacuum (degree of vacuum: −0.098 MPa) for one hour, and then still under vacuum, a 3-minute ultraviolet irradiation (18.5 mW/cm$^2$, 254 nm) was performed to immobilize PAA. Further, the substrate was stirred with ultrapure water for one hour to wash unreacted PAA away and then subjected to spin drying to obtain a substrate for biochips of the present invention.

2. Evaluation

Figure 5:
FIG. 5 shows the measurement results of fluorescence, measured by a fluorescence scanner, from the probe after each of the two washes wherein probe was immobilized on the substrate produced in Example 1 and then washed twice.
Figure 5:
Figure 7:
FIG. 7 shows the measurement results of fluorescence, measured by a fluorescence scanner, from the probe after each of the two washes wherein proteins were immobilized on the substrate produced in Example 1 and then washed twice.
Figure 7:
Figure 8:
FIG. 8 shows the measurement results of fluorescence, measured by a fluorescence scanner, from the probe after each of the two washes wherein proteins were immobilized on the substrate produced in Example 2 and then washed twice.
Figure 8:
Figure 9:
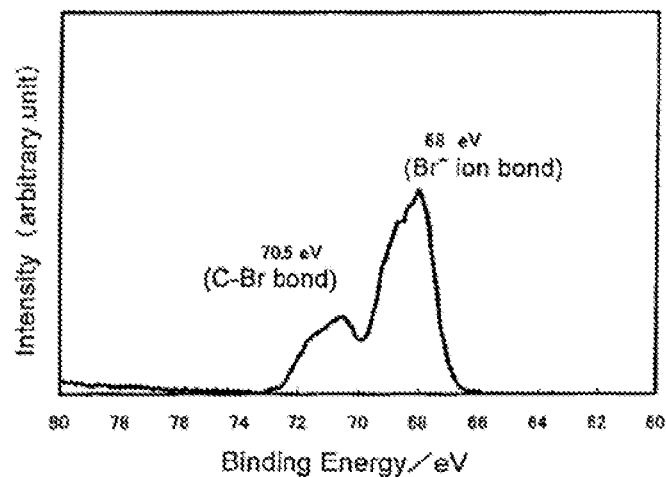
FIG. 9 shows the results of an X-ray photoelectron spectroscopy of the substrate produced in Example 1.

For two substrates produced, uniformity of the amount of amino groups on the surface of the substrate was evaluated (FIG. 1a,b) by the above-described method. The distribution of the amino groups was evaluated by histogram of the dot intensity of the image data (FIG. 2a, b). Amino groups are more uniformly distributed on the PAA coating carbon substrate than on a commercially available aminated glass substrate (below-mentioned Comparative Example 2). Further, the amount of amino groups was calculated by the concentration of free bromide ions. The PAA coated carbon substrate had amino groups on the surface of the substrate at 5.6±0.4 nmol/cm$^2$, and the concentration thereof was higher than that of the below-mentioned aminated glass substrate of Comparative Example 2. The probes immobilized by the above-described method remained immobilized even after the substrate was washed twice (FIG. 5). Further, the degree of adsorption of protein was evaluated by the above-described method and the adsorption of protein (FIG. 7) was smaller than that of the glass substrate of Comparative Example 2 (FIG. 8). Further, an analysis by XPS was carried out and C—Br bonds were observed after amino groups on the surface were bromoacetylated (FIG. 9). By this, it was confirmed that PAA was bound covalently to the surface of the substrate.

Example 2

Aluminum alloy (5000 series alloy) rolled plate (75×25 mm, thickness: 1 mm) was polished with a PVA grindstone to have a surface roughness of Ra 30 nm and then the whole surface of the plate was treated with alkaline degreasing, nitric desmut and zincate processing, and nickel-phosphate electroless plating was applied to the surface at a thickness of 13 µm per one surface. Further, both surfaces of the substrate were polished with an alumina slurry by 3 µm per one surface to attain a surface roughness of 1 nm. Subsequently, SiC was deposited to a thickness of 20 nm hexamethyisiloxane gas by using an ion deposition apparatus on the surface of the substrate, and then DLC was deposited to a thickness of 200 nm in methane gas to coat the surface with carbon to provide substrate material. The polymer was then immobilized in the same manner as in Example 1 to obtain a substrate for biochips.

Example 3

Synthetic quartz slide glass manufactured by Shin-Etsu Chemical Co., Ltd. (75×25 mm, plate thickness: 1 mm) was washed with hydrofluoric acid and then dried under vacuum. Subsequently, the surface of the slide glass was coated with carbon with a thickness of 200 nm in the same method as in Example 2 to provide a substrate material. The polymer was then immobilized on the slide glass in the same manner as in Example 1 to obtain a substrate for biochips.

Example 4

A polymethyl methacrylate plate (75×25 mm, plate thickness: 1 mm) was washed with methanol to provide a substrate material. The polymer was then immobilized on the plate in the same manner as in Example 1 to obtain a substrate for biochip.

Example 5

A polymer solution containing 1% PAA and 0.3% PEG as a hydrophilic polymer in ethanol, as a coating solution, was applied to the surface of an amorphous carbon according to an application method. The polymer was then immobilized on the amorphous carbon in the same manner as in Example 1 to obtain a substrate for biochips.

Comparative Example 1

Figure 2:
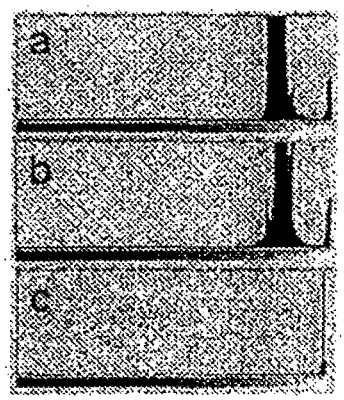
FIG. 2 shows luminance distribution histograms of the surface images shown in FIG. 1.

Amorphous carbon was subjected to ultraviolet treatment (ultraviolet treatment before application of the PAA solution) in the same manner as in Example 1, and then uniformity of the amount of amino groups on the surface of the substrate was evaluated (FIG. 1c). The distribution of the amino groups was evaluated by histogram of the dot intensity of the image data (FIG. 2c). Amino groups were not detected because amino group-containing polymer was not immobilized.

Comparative Example 2

Figure 3:
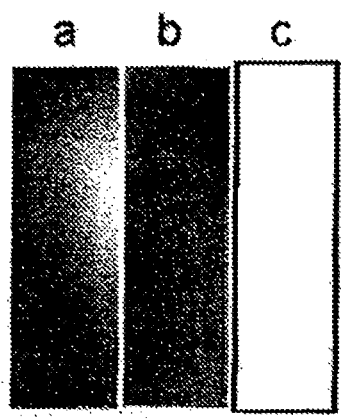
FIG. 3 shows images (a, b) of surfaces which are the surfaces of substrates of Comparative Example 2 modified by a fluorescence labeling which binds to an amino group, and an image (c) of the surface of the substrate of Comparative Example 2 before fluorescence labeling.
Figure 4:
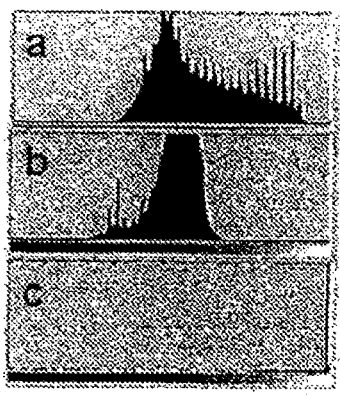
FIG. 4 shows luminance distribution histograms of the surface images shown in FIG. 3.
Figure 6:
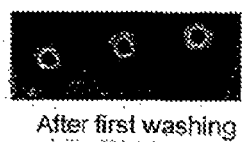
FIG. 6 shows the measurement results of fluorescence, measured by a fluorescence scanner, from the probe after each of the two washes wherein probe was immobilized on the substrate in Example 2 and then washed twice.
Figure 6:
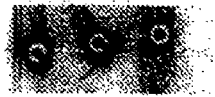

For two kinds of commercially available aminated glass substrates, uniformity of the amount of amino groups on the surface of the substrate was evaluated (FIG. 3). The distribution of the amino groups was evaluated by histogram of the dot intensity of the image data (FIG. 4). The amount of amino groups on the surface of the substrate was non-uniform, and irregularity of the intensity of luminance of the image and the width of histogram were large. Based on the calculation of the amount of amino groups using the concentration of free bromide ions, bromide ions were not detected. This means that covalent immobilization on the glass surface is difficult. Although probes remains as shown in FIG. 6, the image of the probes spreads because the adsorption of a dye is intense and the dye cannot be bound to the substrate covalently. The adsorption of protein was severe as shown in (FIG. 8).

The invention claimed is:

1. A substrate for biochips, comprising:
   (i) a substrate body having a surface composed of carbon;
   (ii) an amino group-containing polymer comprising primary amino groups, the amino group-containing polymer being formed by polymerizing monomers comprising amino group-containing vinyl monomers, and being covalently bound directly to the surface of the substrate body; and
   (iii) a hydrophilic polymer covalently bound directly to the surface of the substrate body,
   wherein the amino group-containing polymer is bound to the carbon substrate in a radical reaction between the carbon surface and an amino group-containing vinyl monomer-derived unit in the amino group-containing polymer, and
   wherein a homogeneous mixture of the amino group-containing polymer and the hydrophilic polymer is immobilized on the surface of the substrate body.

2. The substrate according to claim 1, wherein each of 50% or more of monomeric units which constitute said amino group-containing polymer are derived from monomer(s) having at least one amino group.

3. The substrate according to claim 2, wherein each of 90% or more of the monomeric units which constitute said amino group-containing polymer are derived from the monomer(s) having at least one amino group.

4. The substrate according to claim 1, wherein said amino group-containing polymer is immobilized in an amount such that a density of a number of the primary amino groups in the amino group-containing polymer is $4.22 \times 10^{16}$ amino groups/cm$^2$ or more.

5. The substrate according to claim 4, wherein the amount of said amino group-containing polymer immobilized is 40 μg/cm$^2$ or less.

6. The substrate according to claim 1, wherein said amino group-containing polymer has a weight-average molecular weight such that said amino group-containing polymer has 17 or more primary amino groups per one molecule.

7. The substrate according to claim 6, wherein the weight-average molecular weight of said amino group-containing polymer is 60,000 or less.

8. The substrate according to claim 1, wherein said hydrophilic polymer is at least one selected from the group consisting of polyethylene glycol, polyacrylamide and agarose.

9. The substrate according to claim 1, wherein an amount of said amino group-containing polymer immobilized is such that a density of a number of the primary amino groups in the amino group-containing polymer is $4.22 \times 10^{16}$ amino groups/cm$^2$ or more and said hydrophilic polymer is 40 μg/cm$^2$ or less.

10. The biochip according to claim 1, wherein amino group-containing vinyl monomers constitute 50% or more of the constituent units in the amino group-containing polymer.

11. The biochip according to claim 1, wherein amino group-containing vinyl monomers constitute 90% or more of the constituent units in the amino group-containing polymer.

12. A biochip comprising the substrate of claim 1; and a biologically relevant substance covalently bound directly or via a linker to an amino group of the substrate.

13. The biochip according to claim 12, wherein each of 50% or more of monomeric units which constitute said amino group-containing polymer are derived from monomer(s) having at least one amino group.

14. The biochip according to claim 13, wherein each of 90% or more of the monomeric units which constitute said amino group-containing polymer are derived from the monomer(s) having at least one amino group.

15. The biochip according to claim 12, wherein said amino group-containing polymer is immobilized in an amount such that a density of a number of the primary amino groups in the amino group-containing polymer is $4.22 \times 10^{16}$ amino groups/cm$^2$ or more.

16. The biochip according to claim 15, wherein the amount of said amino group-containing polymer immobilized is 40 μg/cm$^2$ or less.

17. The biochip according to claim 12, wherein said amino group-containing polymer has a weight-average molecular weight such that said amino group-containing polymer has 17 or more primary amino groups per one molecule.

18. The biochip according to claim 17, wherein the weight-average molecular weight of said amino group-containing polymer is 60,000 or less.

19. The biochip according to claim 12, wherein said hydrophilic polymer is at least one selected from the group consisting of polyethylene glycol, polyacrylamide and agarose.

20. The biochip according to claim 12, wherein an amount of said amino group-containing polymer immobilized is such that a density of a number of the primary amino groups in the amino group-containing polymer is $4.22 \times 10^{16}$ amino groups/cm$^2$ or more and the total amount of said amino group-containing polymer and said hydrophilic polymer is 40 μg/cm$^2$ or less.

21. The biochip according to claim 12, wherein the biologically relevant substance is selected from the group consisting of proteins, nucleic acids, peptide derivatives, sugar chains and derivatives thereof, natural products and small molecule compounds.

22. A method of producing the substrate for biochips of claim 1, said method comprising:
    coating the surface of the substrate body with said amino group-containing polymer and said hydrophilic polymer; and subsequently irradiating the surface of the substrate body with light under reduced pressure or under an inert gas atmosphere.

23. A method of producing the substrate for biochips of claim 1, the method comprising:
    a plasma irradiation or a light irradiation on the surface of said substrate body; and subsequently bringing said substrate body into contact with said amino group-containing polymer and said hydrophilic polymer.

24. The method according to claim 23, further comprising a light irradiation on the surface of the substrate body under reduced pressure or under an inert gas atmosphere after bringing said substrate body into contact with said amino group-containing polymer.

* * * * *

```
                              SEQUENCE LISTING

<160> NUMBER OF SEQ ID NOS: 1

<210> SEQ ID NO 1
<211> LENGTH: 17
<212> TYPE: PRT
<213> ORGANISM: Artificial
<220> FEATURE:
<223> OTHER INFORMATION: peptide immobilized on a biochip

<400> SEQUENCE: 1

Gly Leu Gln Gln Leu Ala Arg Ala Leu Arg Arg Leu Ala Gln Ala Gly
1               5                   10                  15

Cys
```